United States Patent [19]

Rossi et al.

[11] Patent Number: 4,812,316

[45] Date of Patent: Mar. 14, 1989

[54] PROCESS FOR THE PREPARATION OF STABILIZED ISOSORBIDE-5-MONONITRATE TABLETS, BEING ALSO OF SUSTAINED RELEASE, AND FORMULATIONS THUS OBTAINED

[75] Inventors: Piergiorgio Rossi, Milan; Massimo Calanchi, Monza, both of Italy

[73] Assignee: Eurand Italia S.p.A., Monza, Italy

[21] Appl. No.: 918,385

[22] Filed: Oct. 14, 1986

[30] Foreign Application Priority Data

Oct. 15, 1985 [IT] Italy ............................... 22493 A/85

[51] Int. Cl.$^4$ ............................................. A61L 15/03
[52] U.S. Cl. ..................................... 424/468; 514/464
[58] Field of Search ........................ 424/468; 514/464

[56] References Cited

U.S. PATENT DOCUMENTS

| | | | |
|---|---|---|---|
| 3,972,995 | 8/1976 | Tsuk et al. | 424/447 |
| 4,291,015 | 9/1981 | Keith et al. | 424/486 |
| 4,482,534 | 11/1984 | Blank | 424/449 |

*Primary Examiner*—Joseph L. Schofer
*Assistant Examiner*—Peter F. Kulkosky
*Attorney, Agent, or Firm*—Gordon W. Hueschen

[57] ABSTRACT

The present invention relates to obtaining isosorbide-5-mononitrate tablets, being also of retard form, which are stable in time. Such embodiment is now possible after the discovery of the stabilizing activity of the with respect to the isosorbide-5-mononitrate with which it forms a solid solution. The use of PVP is essential so that the tablets can remain stable in time: the retard effect in turn can be obtained with the use of hydroxyalkylcelluloses.

12 Claims, No Drawings

PROCESS FOR THE PREPARATION OF STABILIZED ISOSORBIDE-5-MONONITRATE TABLETS, BEING ALSO OF SUSTAINED RELEASE, AND FORMULATIONS THUS OBTAINED

Isosorbide-5-mononitrate is a blood-vessel dilator, the activity of which is above all evident in coronary circulation. As nitroderivatives do generally, it acts to relax the smooth muscles of the cardiovascular system. The active substance is indicated above all in the treatment of the angina syndrome (angina pectoris) arising from coronary insufficiency.

As other nitroderivatives, the isosorbide-5-mononitrate causes, in the greater portion of treated subjects, undesired collateral effects such as headache, cutaneous blood-vessel dilation and somnolence. Considering these negative effects, due to rapidly reaching too elevated a plasmatic level, and furthermore due to the fact that the half-life of the active substance is about 5 hours, the advantages of a form of isosorbide-5-mononitrate having a slow release which is prolonged over a period of time, appear evident.

The use of hydroxypropylmethylcellulose, alone or in mixture with other cellulosic derivatives, for the preparation of matrix tablets with retard effect, is known. For instance, U.S. Pat. No. 4,259,314 relates to the preparation of active substances of retardant effect which is obtained by means of a matrix constituted of a mixture of various types of hydroxypropylmethylcellulose and hydroxypropylcellulose, dried in such a way that the humidity is less than 1% so as to be used with hygroscopic active substances. The U.S. Pat. Nos. 4,369,172 and 4,389,393 also relate to the preparation of tablets of active substances wherein the retard is obtained using a matrix constituted of various types and percentages of hydroxypropylmethylcellulose, alone or in mixture with ethylcellulose and/or sodium carboxymethylcellulose.

Various types of hydroxypropylmethylcellulose are available on the market, among which are those of the Dow Chemical Co., named Methocel E, F, J and K. The names distinguish the differences in methoxy and hydroxypropoxy contents. The percentage by weight of the methoxy groups varies between 17 and 30% while that of the hydroxypropoxy groups varies between 4 and 30%, determined according to the method specified in ASTM D2363-72. Under the various names, Methocel with diverse viscosities is available. The viscosity varies between 5 and 100,000 cps, with reference to aqueous solutions of a product of a 2% concentration and effecting the measurement with a viscosimeter Ubelohde at 20° C.

During the research involved in attaining a retard formulation of isosorbide-5-mononitrate, it was observed how the retard tablets of the active substance isosorbide-5-mononitrate prepared with mixtures of various types of hydroxypropylmethylcellulose, alone or with the other cellulosic derivatives described in the hereinbefore-mentioned patents, are not stable: the hardness of the tablets decreased rapidly with time until reaching practically unacceptable levels with consequent increase of friability. The tablets are therefore useless in that they crumble at the moment of use and present insuperable problems during preparation. It has been found that only by adding, to the traditional excipients including hydroxypropylmethylcellulose, a suitable quantity of polyvinylpyrrolidone (PVP), is it possible to obtain tablets of isosorbide-5-mononitrate which are stable over an extended period of time, and this is also true in the case of formulations with sustained release. This is because the PVP acts not only as binder of the components, including the matrix which imparts the retardant effect to the isosorbide-5-mononitrate tablets, but also forms a solid, stable solution with the isosorbide-5-mononitrate. In fact, the thermic differential analysis has proved that interaction occurs between phases with cryoscopic lowering of the melting point of the mixture with respect to the melting point of the single components.

It was furthermore found that in tablets already on the market, the isosorbide-5-mononitrate tends to migrate from the interior towards the surface and produces sublimation phenomena, forming long filaments when the tablets are placed in closed containers. Such phenomena is evident above all when the tablets are kept at a temperature of 40°-50° C. These phenomena are not observed when isosorbide-5-mononitrate tablets are prepared with polyvinylpyrrolidone, both when the tablets are of rapid effect and when they are of sustained effect, meaning both in the case wherein the tablets do not contain retardant agent (hydroxypropylmethylcellulose) and in those cases wherein it is present. The present invention therefore relates to the formulation of a solid solution between isosorbide-5-mononitrate and polyvinylpyrrolidone in both retard and non-retard, e.g., rapid effect, tablets.

The process for the preparation of retard tablets of the present invention consists, therefore, of the steps of compressing the active substance isosorbide-5-mononitrate in admixture with hydroxypropylmethylcellulose, alone or with other cellulose derivatives which are retardant agents, and with polyvinylpyrrolidone, plus other inert excipients and lubricants commonly use in the preparation of tablets.

The isosorbide-5-mononitrate may be used as such, but is preferably mixed beforehand, for 15 minutes, in a cubic mixer or other equivalent apparatus, with colloidal silica, levilite, or lactose with the aim of increasing the flowability of the active principle and therefore obtaining, in the successive mixing with the other excipients, a more homogeneous dispersion which results in greater precision in dosing of the active substance. This mixture is passed through a 35 mesh ASTM sieve (having mesh openings of 500 microns) and the other components of the formulation are added, namely:

the substances which impart the retard effect in quantities varying between 20 and 80% of the tablet weight. They are generally mixed together before-hand;

the polyvinylpyrrolidone, which forms the solid solution with the isosorbide-5-mononitrate and acts as binder, in ratio with the isosorbide-5-mononitrate varying between 1:5 and 5:1, and preferably between 1:2 and 2:1;

other inert excipients and/or lubricants which improve the physical qualities both of the mixture to be compressed and of the finished tablets.

The substances used to obtain the retard effect, cited as non-limiting examples, are hydroxypropylmethylcellulose, named Methocel, either singly or mixed together in various combinations of type and quality. The hydroxypropylmethylceluloses may, in turn, be mixed with other cellulose derivatives, in a maximum quantity of 30%, such as for example, hydroxypropylcellulose, ethylcellulose, and carboxymethylcellulose. These mixtures may preferably be dried up to a humidity content less than 1%.

Among the inert excipients which can be used, sucrose, fructose, lactose, mannitol, pentaerytrite, levilite, colloidal silica, maize starch, tribasic calcium phosphate, and dibasic calcium phosphate granulate, are cited as non-limiting examples.

Among the lubricants, magnesium stearate, stearic acid, and polyethylene glycols are cited as non-limiting examples. In all the examples illustrated hereafter, the tablets have been prepared with a rotating compressor machine Ronchi AM13 ™, using two types of punches, according to the weight of the tablets, in both cases ovalized with fracture line on both faces; the smallest punch with dimensions 15 mm by 6 mm and the largest punch 19 mm by 9.5 mm.

The release _invitro_ of the tablets was determined by using the rotating blade method, described in the American Pharmacopoea (USP), XXI Edition, page 1244, using 500 ml of artificial gastric juice (pH 1.2). In all examples, immediately after preparation the tablets slowly released the isosorbide-5-mononitrate in a period of 8 hours or more, and the release initially determined remained unvaried for 12 months. This is also independent of the pH, it being found that the quantity of active substance released at pH 1.2 is the same as that released at pH 6.8.

The hardness of the tablets was determined with the apparatus Erweka TBH 28 ™, and the friability with the apparatus Erweka Friabilator ™, determining the percentage of weight lost by 10 tablets after 4 minutes of rotation.

EXAMPLE 1

Non-retard isosorbide-5-mononitrate tablets containing polyvinylpyrrolidone (PVP) were, prepared, having the following composition:

| No | Components | g | mg/tablet |
|---|---|---|---|
| 1 | Isosorbide-5-mononitrate | 400 | 40 |
| 2 | powdered lactose | 1100 | 110 |
| 3 | maize starch | 400 | 10 |
| 4 | Levilite | 15 | 1,5 |
| 5 | Cab-O-Sil M 5 | 15 | 1,5 |
| 6 | Magnesium stearate | 50 | 5 |
| 7 | Polyvinylpyrrolidone | 320 | 32 |

Then, tablets having the same composition were prepared, but without the polyvinylpyrrolidone which was substituted by an equal quantity of lactose.

In this case, wherein the tablets are of the non retard type, no dramatic difference in stability between tablets with and without polyvinylpyrrolidone was observed, as can be seen in the data reported in the following tables but, whereas the tablet samples without PVP, kept at 40° C. for two weeks, showed the formation of long filaments in the interior of the container, indicative of the migration and sublimation of the isosorbide-5-mononitrate, on the contrary the tablet samples with PVP, kept under the same conditions, did not show any of the hereinbefore-mentioned drawbacks.

| | Tablets with PVP | | Tablets without PVP | |
|---|---|---|---|---|
| | 0 | 12 months at room temperature | 0 | 12 months at room temperature |
| Hardness, Kg | 9-11 | 11-12 | 9-11 | 8-10 |
| friability, % | 0.14 | 0.2 | 0.15 | 0.5 |

EXAMPLE 2

Isosorbide-5-mononitrate tablets using sustained release were prepared with a formulation similar to that of Example 3 of U.S. Pat. No. 4,259,314, and precisely:

| No | Components | g | mg/tablet |
|---|---|---|---|
| 1 | Isosorbide-5-mononitrate | 40 | 40 |
| 2 | Methocel E 50 | 200 | 200 |
| 3 | Methocel E 4M | 75 | 75 |
| 4 | Hydroxypropylcellulose | 25 | 25 |
| 5 | Anhydrous lactose | 65 | 65 |
| 6 | Stearic acid | 6 | 6 |
| 7 | Magnesium stearate | 6 | 6 |
| 8 | Syloid 244 | 3 | 3 |

The two types of Methocel and the hydroxypropylcellulose were mixed in advance and dried until a humidity content less than to 1%.

The hardness and the friability of the tablets were determined, obtaining results initially satisfying but, after 12 months of storage, the hardness had decreased and the friability increased to such values as to exclude their use. The values found are reported in the following table:

| Tablets without PVP | initial | after 12 months at room temperature |
|---|---|---|
| Hardness, kg | 6.0-8.0 | 1.0-3.0 |
| friability, % | 0.18 | >10 |

The phenomenon is very evident at more elevated temperatures: the tablets in a glass flask were placed in an oven at 40° C.; the hardness and friability were determined on samples taken after 1, 2 and 3 months. The values found, reported in the following table, show the rapid and negative variation of the characteristics of the tablets.

| Tablets without PVP | 0 | 1 | 2 | 3 months |
|---|---|---|---|---|
| | | at 40° C. | | |
| hardness, kg | 8.0 | 7.8 | 6.6 | 4.0 |
| friability, % | 0.3 | 1.2 | 3.2 | >10 |

Adding to the same formulations 40 g of polyvinylpyrrolidone, tablets were obtained which maintain their characteristics in time, namely:

| Tablets with PVP | initial | after 12 months at room temperature |
|---|---|---|
| hardnes, kg | 12-13 | 13-14 |
| friability, % | 0.18 | 0.14 |

This result is confirmed by that obtained on the samples of tablets steadily placed at 40° C., the data of which is reported in the following table:

| Tablets with PVP | 0 | 1 | 2 | 3 months |
|---|---|---|---|---|
| | | at 40° C. | | |
| hardness, kg | 12.3 | 19.8 | 19.4 | 19.3 |
| friability, % | 0.14 | 0.10 | 0.10 | 0.10 |

EXAMPLE 3

Isosorbide-5-mononitrate tablets of sustained release were prepared using a formulation very similar to that of Example 3 of U.S. Pat. No. 4,389,393, namely:

| No | Components | g | mg/tablet |
|---|---|---|---|
| 1 | Isosorbide-5-mononitrate | 160 | 80 |
| 2 | Methocel K 4M | 112 | 56 |
| 3 | Methocel K 15M | 48 | 24 |
| 4 | Anhydrous lactose | 480 | 240 |
| 5 | Stearic acid | 12 | 6 |
| 6 | Syloid 244 | 6 | 3 |

The components 2 and 3 were mixed in advance, as were the ingredients 1 and 4. These two mixtures were combined and mixed again for 15 minutes. After having sieved the resulting mixture through a 20 mesh sieve (ASTM), the ingredients 5 and 6 were added, and mixing was effected for another 20 minutes, whereafter the tablets were made. The hardness and the friability were determined, obtaining results initially satisfying, but utterly negative after 12 months of storing at room temperature, as the following data show:

| Tablets without PVP | initial | after 12 months at room temperature |
|---|---|---|
| hardness, kg | 12–14 | 1.5–3.5 |
| friability, % | 0.16 | >10 |

Tablets prepared using the same formulation with an extra 150 g of polyvinylpyrrolidone (equal to 75 mg/tablet) maintained the initial satisfying characteristics, as the following data show:

| Tablets with PVP | initial | after 12 months at room temperature |
|---|---|---|
| hardness, kg | 13–14 | 14–15 |
| friability, % | 0.13 | 0.17 |

EXAMPLE 4

Isosorbide-5-mononitrate tablets of sustained release were prepared using the following formulation:

| No | Components | g | mg/tablet |
|---|---|---|---|
| 1 | Isosorbide-5-mononitrate | 160 | 40 |
| 2 | Methocel E 50 | 600 | 150 |
| 3 | Methocel E 4M | 380 | 95 |
| 4 | Hydroxypropylcellulose | 120 | 30 |
| 5 | Anhydrous lactose | 64 | 16 |
| 6 | Tribasic calcium phosphate | 14 | 3,5 |
| 7 | Ployethylene glycol | 20 | 5 |
| 8 | Levilite | 12 | 3 |
| 9 | Magnesium Stearate | 20 | 5 |
| 10 | Polyvinylpyrrolidone | 130 | 32,5 |

Tablets having the same composition were also prepared but without polyvinylpyrrolidone, which was replaced by an equal quantity of lactose.

Whereas the tablets containing polyvinylpyrrolidone keep their properties of hardness and friability unaltered in time, those without polyvinylpyrrolidone become friable and therefore practically useless. The data found at the beginning and after 12 months are reported in the following table:

| | Tablets with PVP | | Tablets without PVP | |
|---|---|---|---|---|
| | 0 | 12 months at room temperature | 0 | 12 months at room temperature |
| hardness, kg | 11–13 | 12–14 | 7–9 | 2–4 |
| friability, % | 0.1 | 0.1 | 0.2 | >10 |

EXAMPLE 5

Isosorbide-5-mononitrate tablets of sustained release were prepared according to the following formulation:

| No | Components | g | mg/tablet |
|---|---|---|---|
| 1 | Isosorbide-5-mononitrate | 800 | 80 |
| 2 | Methocel E 50 | 2600 | 260 |
| 3 | Methocel E 4M | 2100 | 210 |
| 4 | Hydroxypropylcellulose | 600 | 60 |
| 5 | Powdered anhydrous lactose | 320 | 32 |
| 6 | Maize starch | 200 | 20 |
| 7 | Ployerthylene glycol | 170 | 17 |
| 8 | Cab-O-Sil M 5 | 60 | 6 |
| 9 | Magnesium stearate | 100 | 10 |
| 10 | Polyvinylpyrrolidone | 650 | 65 |

The component 1 was mixed together with the components 5 and 8 for 15 minutes in a cubic mixer. The mixture was sieved with a 35 mesh sieve (ASTM): mixture A. Separately, another mixture was made with components 2, 3 and 4, mixing for 15 minutes in a cubic mixer. To this mixture, sieved through a 16 mesh sieve (ASTM), the components 6, 7, 9 and 10 were added and mixing continued for another 15 minutes, and the mixture thereafter sieved with a 35 mesh sieve (ASTM): mixture B. The mixture A was combined with the mixture B and mixed for 20 minutes. Then tablets were prepared and had the characteristics reported in the following table:

| Tablets with PVP | initial | after 12 months at room temperature |
|---|---|---|
| hardness, kg | 13–15 | 14–16 |
| friability, % | 0.04 | 0.1 |

Tablets having the same composition were also prepared, but without the polyvinylpyrrolidone, and these showed a decrease of the hardness, and consequent increase of friability, after a year at room temperature, as can be seen in the following table:

| Tablets without PVP | initial | after 12 months at room temperature |
|---|---|---|
| hardness, kg | 6–8 | 1–3 |
| friability, % | 0.2 | >10 |

EXAMPLE 6

Isosorbide-5-mononitrate tablets of sustained release were prepared according to the following formulation:

| No | Components | g | mg/tablet |
|---|---|---|---|
| 1 | Isosorbide-5-mononitrate | 300 | 60 |
| 2 | Methocel E 50 | 667 | 133.4 |
| 3 | Methocel E 4M | 416,5 | 83.3 |
| 4 | Hydroxypropycellulose | 166.5 | 33.3 |
| 5 | Maize starch | 50 | 10 |
| 6 | Cab-O-Sil M 5 | 15 | 3 |
| 7 | Magnesium stearate | 15 | 3 |
| 8 | Anhydrous lactose | 160 | 32 |
| 9 | Polyvinylpyrrolidone | 160 | 32 |

The component 1 was mixed together with the components 6 and 8 for 15 minutes. Another mixture was made with the components 2, 3 and 4. The remaining components were added to this mixture, and mixing was continued for another 15 minutes. Finally, the first mixture was also added, and mixing was continued for another 20 minutes, whereafter tablets were prepared having the following characteristics:

| Tablets with PVP | initial | after 12 months at room temperature |
|---|---|---|
| hardness, kg | 7.5–9.5 | 8–10 |
| friability, % | 0.15 | 0.16 |

Also in this case, tablets having the same composition were made in the same manner, but without the polyvinylpyrrolidone, but were relatively unstable as the following data show:

| Tablets without PVP | initial | after 12 months at room temperature |
|---|---|---|
| hardness, kg | 7–9 | 2–4 |
| friability, % | 0.16 | >10 |

We claim:

1. Pharmaceutical formulation suitable for preparation of tablets for oral administration and release in the stomach which exhibit improved stability, hardness, and friability over an extended period as contrasted with tablets not containing polyvinylpyrrolidone (PVP), characterized by containing, besides excipients usually used in the preparation of tablets, isosorbide-5-mononitrate, in a therapeutically-effective dose, and (a) one or more types of hydroxypropylmethylcellulose in a quantity between about 20 and 80 percent of the tablet weight; and (b) polyvinylpyrrolidone (PVP) in a weight ratio with the isosorbide-5-mononitrate between about 1:5 and 5:1.

2. One or more pharmaceutical formulation according to claim 1, characterized by the fact that other cellulose derivatives are present in addition to the hydroxypropylmethylcellulose, up to a maximum of 30% by weight of the quantity of the hydroxypropylmethylcellulose.

3. Pharmaceutical formulation according to claim 2, characterized by the fact that the cellulose derivative added is hydroxypropylcellulose.

4. Pharmaceutical formulation according to claim 1, characterized by the fact that the hydroxypropylmethylcellulose has a viscosity between 50 and 100,000 centipoise in a 2% water solution at 20° C. by weight and a percentage of methoxy groups between 17 and 30% and a percentage by weight of hydroxyproproxy groups between 4 and 30%.

5. Pharmaceutical tablet for oral administration and release in the stomach containing a pharmaceutical formulation as specified in claim 1.

6. Process for the preparation of a pharmaceutical formulation according to claim 1, characterized by the fact that the active ingredient, isosorbide-5-mononitrate, is mixed with polyvinylpyrrolidone (PVP) as a binder in order to form a solid solution, and that the said mixture is then compressed to produce tablets, characterized by the further fact that the ratio between the PVP and the isosorbide-5-mononitrate is between about 1:5 and 5:1 by weight, and that additional substances are added to the mixture in a quantity between about 20 and 80 percent by weight of the tablet, such additional substances being hydroxypropylmethylcellulose, alone or with another cellulose derivative selected from the group consisting of hydroxypropylcellulose, ethylcellulose, and carboxymethylcellulose.

7. Process according to claim 6, characterized by the fact that the isosorbide-5-mononitrate, before blending with other components of the formulation, is mixed with an agent which increases the flowability of the active principle selected from colloidal silica, levilite, and lactose.

8. Process according to claim 8, characterized by the fact that other inert excipients and/or lubricants, which improve the physical qualities both of the mixture to be compressed and the finished tablets, are added to the mixture to be compressed.

9. Process according to claim 8, characterized by the fact that a compound selected from magnesium stearate, stearic acid, and polyethylene glycol is used as lubricant.

10. Pharmaceutical formulation of claim 1, wherein the ratio is between 1:2 and 2:1.

11. Process of claim 6, wherein the ratio is between 1:2 and 2:1.

12. Process of claim 6, wherein retard substances are mixed together with the other tablet ingredients in advance of tablet compression.

* * * * *

UNITED STATES PATENT AND TRADEMARK OFFICE
CERTIFICATE OF CORRECTION

PATENT NO. : 4,812,316

DATED : March 14, 1989     Page 1 of 2

INVENTOR(S) : Piergiorgio Rossi and Massimo Calanchi

It is certified that error appears in the above-identified patent and that said Letters Patent is hereby corrected as shown below:

Title Page, [57] ABSTRACT, line 4; delete "the" (third occurrence) and insert in its place -- polyvinylpyrrolidone --
Col. 2, line 37; "use" should read -- used --
Col. 2, lines 64&65; "hydroxpropylmethylcelluloses" should read -- hydroxypropylmethylcelluloses --
Col. 3, line 12; "AM13 TM," should read -- AM13 (TM), --

Col. 3, line 14; "with fracture line" should read -- with a fracture line --
Col. 3, line 17; "invitro" should read -- in vitro --

Col. 3, line 29; "TBH 28 TM," should read -- TBH 28 (TM), --

Col. 3, line 30; "Friabilator TM," should read -- Friabilator (TM), --

Col. 4, line 28; delete "to"
Col. 4, line 63; "hardnes," should read -- hardness, --
Col. 5, line 61; "Ployethylene" should read -- Polyethylene --
Col. 6, line 30; "Ployerthylene" should read -- Polyethylene --
Col. 8, line 1; delete "One or more"
Col. 8, line 1; "pharmaceutical" should read -- Pharmaceutical --
Col. 8, line 2; after "that" insert -- one or more --
Col. 8, line 13; delete "by weight"
Col. 8, line 14; after "percentage" insert -- by weight --

UNITED STATES PATENT AND TRADEMARK OFFICE
CERTIFICATE OF CORRECTION

PATENT NO. : 4,812,316

DATED : March 14, 1989

INVENTOR(S) : Piergiorgio Rossi and Massimo Calanchi

It is certified that error appears in the above-identified patent and that said Letters Patent is hereby corrected as shown below:

Col. 8, line 15; "hydroxyproproxy" should read -- hydroxypropoxy --
Col. 8, line 41; "claim 8," should read -- claim 6, --

Signed and Sealed this

Seventeenth Day of October, 1989

Attest:

DONALD J. QUIGG

Attesting Officer

Commissioner of Patents and Trademarks